US012667595B2

(12) United States Patent
Kim et al.

(10) Patent No.: US 12,667,595 B2
(45) Date of Patent: Jun. 30, 2026

(54) COMPOSITION FOR PREVENTING, IMPROVING OR TREATING BENIGN PROSTATIC HYPERPLASIA OR ALOPECIA, COMPRISING HEAT-KILLED PROBIOTICS AS ACTIVE INGREDIENT

(71) Applicant: BEREUM CO., LTD, Wonju-si (KR)

(72) Inventors: Eun Kyung Kim, Chungju-si (KR);
Kwon Il Han, Wonju-si (KR);
Masahiro Iwasa, Wonju-si (KR);
Young Jin Choi, Hwaseong-si (KR);
Meiqi Fan, Chungju-si (KR)

(73) Assignee: BEREUM CO., LTD, Wonju-si (KR)

( * ) Notice: Subject to any disclaimer, the term of this patent is extended or adjusted under 35 U.S.C. 154(b) by 472 days.

(21) Appl. No.: 18/168,526

(22) Filed: Feb. 13, 2023

(65) Prior Publication Data

US 2023/0190830 A1 Jun. 22, 2023

Related U.S. Application Data

(63) Continuation of application No. PCT/KR2020/017030, filed on Nov. 27, 2020.

(30) Foreign Application Priority Data

Aug. 13, 2020 (KR) ........................ 10-2020-0101590

(51) Int. Cl.
*A61K 35/742* (2015.01)
*A23L 33/135* (2016.01)
*A61P 13/08* (2006.01)
*A61P 17/14* (2006.01)

(52) U.S. Cl.
CPC .......... *A61K 35/742* (2013.01); *A23L 33/135* (2016.08); *A61P 13/08* (2018.01); *A61P 17/14* (2018.01)

(58) Field of Classification Search
CPC ..... A61K 35/742; A23L 33/135; A61P 13/08; A61P 17/14
See application file for complete search history.

(56) References Cited

U.S. PATENT DOCUMENTS

2008/0063666 A1* 3/2008 Allende .................. A61P 37/00
435/253.4

FOREIGN PATENT DOCUMENTS

| JP | 2004-210659 | A | 7/2004 |
| KR | 10-2009-0051586 | A | 5/2009 |
| KR | 10-2019-0041864 | A | 4/2019 |
| KR | 10-2019-0041865 | A | 4/2019 |
| KR | 10-2019-0081545 | A | 7/2019 |
| KR | 10-2022263 | B1 | 9/2019 |

OTHER PUBLICATIONS

Choi et al. (Nutrients, vol. 8 No. 146, pp. 1-11). (Year: 2016).*
International Search Report & Written Opinion for PCT/KR2020/017030 by Korean Intellectual Property Office dated May 7, 2021.
Office Action for KR10-2020-0101590 by Korean Intellectual Property Office dated Oct. 28, 2021.
Extended European Search Report for EP 20949609.0 by European Patent Office dated Aug. 28, 2024.
Office Action for CN 202080103936.0 by China National Intellectual Property Administration dated Dec. 11, 2024.

* cited by examiner

*Primary Examiner* — Robert A Zeman
(74) *Attorney, Agent, or Firm* — BROADVIEW IP LAW, PC

(57) ABSTRACT

Provided is a pharmaceutical composition for preventing or treating benign prostatic hyperplasia or alopecia, comprising lactic acid bacteria of *Enterococcus* genus as an active ingredient. The pharmaceutical composition of the present invention can replace the conventional therapeutic agents against treating benign prostatic hyperplasia or alopecia, such as finasteride or dutasteride. In particular, by introducing heat-killed probiotics of *Enterococcus faecalis*, the effect of preventing or treating benign prostatic hyperplasia or alopecia can be further enhanced.

4 Claims, 11 Drawing Sheets

Con                  BPH

BPH+K-EF             BPH+L-EF             BPH+Fi

COMPOSITION FOR PREVENTING, IMPROVING OR TREATING BENIGN PROSTATIC HYPERPLASIA OR ALOPECIA, COMPRISING HEAT-KILLED PROBIOTICS AS ACTIVE INGREDIENT

CROSS-REFERENCE TO RELATED APPLICATIONS

This application is a continuation of pending PCT International Application No. PCT/KR2020/017030, filed on Nov. 27, 2020, which claims priority to Korean Patent Application No. 10-2020-0101590 filed on Aug. 13, 2020, the entire contents of which are hereby incorporated by references in its entirety.

TECHNICAL FIELD

The present invention relates to a composition for preventing, improving or treating benign prostatic hyperplasia or alopecia, comprising lactic acid bacteria as an active ingredient, more specifically, a composition for preventing, improving or treating benign prostatic hyperplasia or alopecia, comprising lactic acid bacteria of the *Enterococcus* genus, in particular, heat-killed probiotics as an active ingredient.

BACKGROUND ART

Prostate disease can be broadly divided into benign prostatic hyperplasia and prostate cancer. Benign prostatic hyperplasia, which is a disease that reduces the rate of urination, occurs mainly after the age of 40 and has a characteristic that the frequency of occurrence is proportional to the increase of age. Therefore, more than 50% of men after 65 years of age have symptomatic benign prostatic hyperplasia, and the occurrence of the symptoms at the lower urinary tract due to benign prostatic hyperplasia reduces the quality of life.

Male hormones play the most important roles in the pathogenesis of these diseases. Dihydrotestosterone is the main male hormone involved in the growth of prostatic tissues, and about 90% of testosterone in the prostate is converted to dihydrotestosterone. Testosterone is also secreted from the adrenal gland, but about 90% of it is a primary male hormone synthesized and secreted by Leydig cells of the testes. In the prostate, testosterone is irreversibly converted by 5-alpha reductase to dihydrotestosterone as a precursor of the hormone. There are two isoforms of 5-alpha reductase that converts testosterone to dihydrotestosterone: type 1 and type 2. The mRNA expression of type 1 and type 2 5-alpha reductase occurs in normal prostate, benign prostatic hyperplasia, and prostate cancer tissues. Type 1 5-alpha reductase is expressed mainly in epithelial cells, while type 2 5-alpha reductase is expressed mainly in stromal cells. Type 2 5-alpha reductase is expressed in some basal epithelial cells, but not in other epithelial cells. Therefore, only type 1 5-alpha reductase is present in epithelial cells of the prostate, and both type 1 and type 2 5-alpha reductase are present in stromal cells.

For this reason, it can be expected that 5-alpha reductase inhibitors can be used in these diseases to exert their ability to inhibit the diseases. The 5-alpha reductase inhibitors used for benign prostatic hyperplasia include finasteride and dutasteride. Of these, finasteride is known to inhibit only type 2 5-alpha reductase, and dutasteride to inhibit both type 1 and type 2 5-alpha reductase. These drugs, which are similar derivatives of 4-azasteroid nucleus, reversibly inhibit the activity of 5-alpha reductase, which is a NADPH-dependent enzyme that converts testosterone to dihydrotestosterone, and thus promote the apoptosis of prostate epithelial cells, thereby inhibiting overgrowth of prostate and reducing prostatic volume. However, such conventional drugs are slow to be absorbed, and side effects of sexual dysfunction may occur.

Another symptom caused by male hormones such as dihydrotestosterone (DHT) is male pattern baldness. Causes of alopecia that have been suggested include poor blood circulation, excessive male hormone activity, excessive sebum secretion, decreased scalp function due to dandruff bacteria and other bacteria, genetic factors, and aging stress. The cause of androgenic alopecia, which is the most common type of alopecia that is directly related to excessive male hormone secretion, has been revealed.

In the case of androgenic alopecia, healthy hair gradually becomes thinner and shorter, and so the hair becomes weak and brittle, which is referred to as miniaturization. Hair follicles that undergo miniaturization eventually become thin and invisible, and the hair is turned into short fuzz, as alopecia continues. Therefore, many studies have been reported recently for the prevention and treatment of alopecia through the inhibition of male hormone activity.

Testosterone is converted by 5α-reductase to dihydrotestosterone (DHT), an active male hormone, and the activated dihydrotestosterone binds to androgen receptors to impede protein synthesis by follicular cells. Consequently, the growth period of hair follicles is shortened, and the hair follicles are shrunken, resulting in alopecia. In addition, excessive production of sebum sometimes occurs in the process of androgenic alopecia, leading to alopecia accompanied by inflammation on the scalp.

Therefore, there is a need for a drug that can be rapidly absorbed and that can exhibit excellent effects while minimizing side effects in order to replace finasteride or dutasteride.

DETAILED DESCRIPTION OF THE INVENTION

Technical Problem

An object of the present invention is to provide a pharmaceutical composition for preventing or treating benign prostatic hyperplasia or alopecia, comprising lactic acid bacteria of *Enterococcus* genus, in particular, heat-killed probiotics as an active ingredient, which is capable of inhibiting the expression of androgen receptor (AR) signaling factors including androgen receptor (AR), estrogen receptors (ER), and prostate specific antigen (PSA); apoptosis inhibiting factors including Bcl-2; and cell proliferation factors including proliferating cell nuclear antigen (PCNA) and cyclin D1.

Another object of the present invention is to provide a food composition for preventing or improving benign prostatic hyperplasia or alopecia, comprising lactic acid bacteria of *Enterococcus* genus, in particular, heat-killed probiotics as an active ingredient, which is capable of inhibiting the expression of androgen receptor (AR) signaling factors including androgen receptor (AR), estrogen receptors (ER), and prostate specific antigen (PSA); apoptosis inhibiting factors including Bcl-2; and cell proliferation factors including proliferating cell nuclear antigen (PCNA) and cyclin D1.

Technical Solution

According to an aspect of the present invention, there is provided a pharmaceutical composition for preventing or treating benign prostatic hyperplasia or alopecia, comprising lactic acid bacteria of *Enterococcus* genus as an active ingredient.

The lactic acid bacteria of *Enterococcus* genus may be at least one selected from *Enterococcus faecalis* and *Enterococcus faecium*.

The lactic acid bacteria of *Enterococcus* genus may be at least one type of heat-killed probiotics selected from *Enterococcus faecalis* and *Enterococcus faecium*.

The lactic acid bacteria of *Enterococcus* genus may be heat-killed probiotics of *Enterococcus faecalis* EF-2001.

The pharmaceutical composition may be for inhibiting the expression of an androgen receptor (AR) signaling factor, which is any one selected from estrogen receptors (ER), androgen receptor (AR), and prostate specific antigen (PSA).

The pharmaceutical composition may be for promoting the expression of Bax, which is an apoptosis inducing factor, and/or for inhibiting the expression of Bcl-2, which is an apoptosis inhibiting factor.

The pharmaceutical composition may be for inhibiting the expression of any one cell proliferation factor selected from proliferating cell nuclear antigen (PCNA) and Cyclin D1.

Advantageous Effects

The composition for preventing, improving or treating benign prostatic hyperplasia or alopecia of the present invention, comprising lactic acid bacteria of *Enterococcus* genus, particularly, heat-killed probiotics, as an active ingredient, has an effect of inhibiting the expression of androgen receptor (AR) signaling factors including androgen receptor (AR), estrogen receptors (ER), and prostate specific antigen (PSA); apoptosis inhibiting factors including Bcl-2; and cell proliferation factors including proliferating cell nuclear antigen (PCNA) and cyclin D1.

MODE OF THE INVENTION

Figure 1:
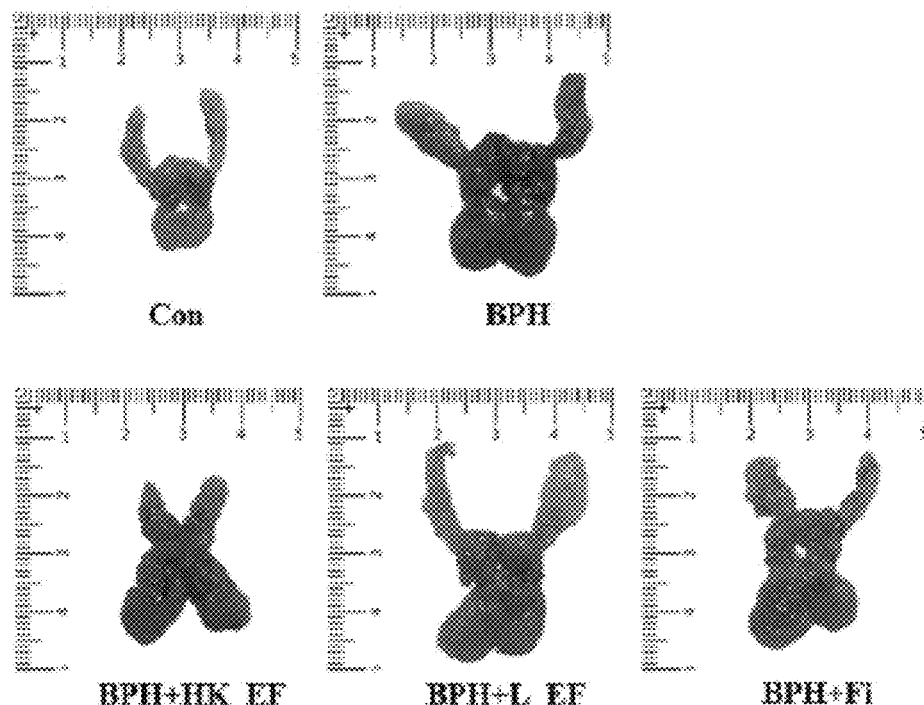
FIG. 1 is a photograph of the prostate according to Experimental Example 1.

Hereinafter, various aspects and various embodiments of the present invention will be described in more detail.

Hereinafter, Examples of the present invention will be described in detail with reference to the accompanying drawings so that one of ordinary skill in the art can easily implement the present invention.

However, the following description is not intended to limit the present invention to specific embodiments, and when it is determined that a detailed description of a related known technology may obscure the gist of the present invention in describing the present invention, the detailed description will be omitted.

The terminology used herein is used only to describe specific Examples, and is not intended to limit the present invention. The singular expression includes the plural expression unless the context clearly dictates otherwise. In the present application, terms such as "comprise" or "have" are intended to designate that a feature, number, step, operation, element, or combination thereof described in the specification exists, and they should be understood as not precluding in advance the possibility of the presence or addition of one or more other features or numbers, steps, operations, elements, or combinations thereof.

The pharmaceutical composition for preventing or treating benign prostatic hyperplasia or alopecia of the present invention comprises lactic acid bacteria of *Enterococcus* genus as an active ingredient.

The lactic acid bacteria of *Enterococcus* genus is preferably at least one selected from among *Enterococcus faecalis* and *Enterococcus faecium*.

More preferably, the lactic acid bacteria of *Enterococcus* genus may be one or more type of heat-killed probiotics selected from *Enterococcus faecalis* and *Enterococcus faecium*.

Even more preferably, the lactic acid bacteria of *Enterococcus* genus may be heat-killed probiotics of *Enterococcus faecalis* EF-2001.

The pharmaceutical composition may be for inhibiting the expression of an androgen receptor (AR) signaling factor, which is any one selected from estrogen receptors (ER), androgen receptor (AR) and prostate specific antigen (PSA).

In addition, the pharmaceutical composition may be for promoting the expression of Bax, which is an apoptosis inducing factor, and/or for inhibiting the expression of Bcl-2, which an apoptosis inhibiting factor.

In addition, the pharmaceutical composition may be for inhibiting the expression of a cell proliferation factor, which is any one selected from proliferating cell nuclear antigen (PCNA) and Cyclin D1.

The probiotics of *Enterococcus* genus may be not only probiotics or heat-killed probiotics itself but also one prepared in a powder state by an additional process such as freeze-drying or spray-drying.

As used herein, the term 'comprising as an active ingredient' means comprising an amount sufficient to achieve the efficacy or activity of lactic acid bacteria of *Enterococcus* genus. In one embodiment of the present invention, the lactic acid bacteria of *Enterococcus* genus in the composition of the present invention is, for example, 0.001 mg/kg or more, preferably 0.1 mg/kg or more, more preferably 10 mg/kg or more, even more preferably 100 mg/kg or more, even more preferably 250 mg/kg or more, and most preferably 1 g/kg or more. The upper quantitative limit of the lactic acid bacteria of *Enterococcus* genus can be implemented by one of ordinary skill in the art by selecting within an appropriate range without side effects.

The pharmaceutical composition of the present invention may be prepared by using a pharmaceutically suitable and physiologically acceptable adjuvant in addition to the active ingredient, and as the adjuvant, an excipient, a disintegrant, a sweetener, a binder, a coating agent, a swelling agent, a lubricant, a glydent or a flavoring agent, etc. may be used.

The pharmaceutical composition may be preferably formulated as a pharmaceutical composition by including one or more pharmaceutically acceptable carriers in addition to the active ingredients described above for administration.

Formulations of the pharmaceutical composition may be granule, powder, tablet, coated tablet, capsule, suppository, solution, syrup, juice, suspension, emulsion, drop or injectable. For example, for formulation in the form of a tablet or capsule, the active ingredient may be combined with an orally administered, non-toxic, pharmaceutically acceptable inert carrier such as ethanol, glycerol, water, and the like. In addition, if desired or needed, suitable binders, lubricants, disintegrants, and color development agents may also be included in the mixture. Suitable binders include, but are not limited to, starch, gelatin, natural sugars such as glucose or beta-lactose, corn sweeteners, natural and synthetic gums such as acacia, tragacanth and sodium oleate, sodium stearate, magnesium stearate, sodium benzoate, sodium acetate, sodium chloride, and the like. Disintegrants include, but are not limited to, starch, methyl cellulose, agar, bentonite, xanthan gum, and the like.

In the composition formulated as a liquid solution, as acceptable pharmaceutical carriers that are sterile and biocompatible, saline, sterile water, Ringer's solution, buffered saline, albumin injection, dextrose solution, maltodextrin solution, glycerol, ethanol, and a mixture of one or more of these components may be mixed and used, and other conventional additives such as antioxidants, buffers, and bacteriostats may be added according to the need. In addition, diluents, dispersants, surfactants, binders, and lubricants may be additionally added to formulate an injectable formulation such as an aqueous solution, suspension, emulsion and so on, pills, capsules, granules or tablets.

The pharmaceutical composition of the present invention may be administered orally or parenterally, and in the case of parenteral administration, it may be administered by intravenous injection, subcutaneous injection, intramuscular injection, intraperitoneal injection, transdermal administration, and so on, preferably by oral administration.

A suitable dosage of the pharmaceutical composition of the present invention varies depending on factors such as formulation method, administration mode, and the age, weight, pathological conditions, food, administration time, administration route, excretion rate, and response sensitivity of the patient, and an ordinarily skilled physician can easily determine and prescribe an effective dosage for the desired treatment or prevention. According to a preferred embodiment of the present invention, the daily dose of the pharmaceutical composition of the present invention is 0.001-10 g/kg.

The pharmaceutical composition of the present invention is prepared in unit dosage form by formulating the same by using a pharmaceutically acceptable carrier and/or excipient according to a method that can be easily implemented by one of ordinary skill in the art to which the present invention pertains, or it may be prepared by being introduced into a multi-dose container. At that time, the formulation may be in the form of a solution, suspension, or emulsion in oil or aqueous medium, or may be in the form of an extract, powder, granule, tablet or capsule, and may further comprise a dispersant or stabilizer.

In addition, the present invention provides a food composition for preventing or improving benign prostatic hyperplasia or alopecia, comprising lactic acid bacteria of *Enterococcus* genus as an active ingredient.

The specific description of the lactic acid bacteria of genus *Enterococcus* and the food composition is the same as the description of the pharmaceutical composition for preventing or treating benign prostatic hyperplasia or alopecia, comprising the lactic acid bacteria of genus *Enterococcus* as an active ingredient, and so the details are referred to the part.

The food composition according to the present invention may be formulated in the same manner as the pharmaceutical composition to be used as a functional food or added to various types of food. Foods to which the composition of the present invention can be added include, for example, beverages, alcoholic beverages, confectionery, diet bars, dairy products, meat, chocolate, pizza, ramen, other noodles, gums, ice cream, composite vitamins, health supplements, and so on.

The food composition of the present invention may include not only the active ingredients but also ingredients that are commonly added during food production, for example, proteins, carbohydrates, fats, nutrients, seasonings and flavoring agents. Examples of the above-mentioned carbohydrates include monosaccharides such as glucose, fructose, and the like; disaccharides such as maltose, sucrose, oligosaccharides, and the like; and polysaccharides, for example, conventional sugars such as dextrin, cyclodextrin, and the like, and sugar alcohols such as xylitol, sorbitol, and erythritol. As flavoring agents, natural flavoring agents [thaumatin, *stevia* extract (for example, rebaudioside A, glycyrrhizin, etc.)] and synthetic flavoring agents (saccharin, aspartame, etc.) can be used. For example, when the food composition of the present invention is prepared as a drink or beverage, in addition to voratin of the present invention citric acid, liquid fructose, sugar, glucose, acetic acid, malic acid, fruit juice, and various plant extracts may be further included.

The present invention provides a health functional food comprising a food composition for preventing or improving benign prostatic hyperplasia or alopecia, comprising the lactic acid bacteria of *Enterococcus* genus as an active ingredient. A health functional food refers to a food prepared by adding lactic acid bacteria of *Enterococcus* genus to food materials such as beverage, teas, spices, gums, and confectionery, or by preparing as capsule, powder, or suspension, etc., which, when ingested, brings about a specific health effect. However, unlike general drugs, a health functional food, which is prepared by using food as a raw material, has the advantage of not causing side effects that may occur when taking a drug for a long time. The health functional food of the present invention obtained in this way is very useful, because it can be ingested routinely. The amount of lactic acid bacteria of *Enterococcus* genus may not be uniformly defined, because it is different depending on the type of health functional food, but the lactic acid bacteria of *Enterococcus* genus may be added within a range that does not impair the original taste of the food, usually in a range of 0.01% to 50% by weight, preferably 0.1% to 20% by weight of the subject food. In addition, a health functional food in the form of pills, granules, tablets or capsules, may commonly be added in an range of 0.1% to 100% by weight, preferably 0.5% to 80% by weight. In one embodiment, the health functional food of the present invention may be in the form of pills, tablets, capsules or beverage.

Hereinafter, the present invention will be described in detail with Examples.

EXAMPLE

Example 1: Preparation of Heat-Killed Probiotics of *Enterococcus faecalis*

The heat-killed probiotics of *Enterococcus faecalis* EF-2001 was commercial probiotics and isolated from feces of healthy people. In addition, it was purchased from Bereum Korea Inc. as a dried powder after being killed by heat. The dried EF-2001 included $7.5 \times 10^{12}$ colonies per gram.

Example 2: Preparation of Probiotics of *Enterococcus Faecalis*

The probiotics of *Enterococcus faecalis* EF-2001 included $1 \times 10^{11}$ colonies per gram.

Experimental Example

Animal Model

After acclimatization of 10-week old male Wister rats for 1 week, a model was created by using the following experimental group.

Con: Normal group

BPH: Benign prostatic hyperplasia induced group

BPH+K_EF: Group of benign prostatic hyperplasia+treatment with heat-killed probiotics of *Enterococcus faecalis*

BPH+L_EF: Group of benign prostatic hyperplasia+treatment with probiotics of *Enterococcus faecalis*

BPH+Fi: Benign prostatic hyperplasia+treatment with finasteride

Specifically, the normal group (Con) was prepared by subcutaneous injection of corn oil and treatment with water.

The benign prostatic hyperplasia induced group (BPH) consisted of castrated rats prepared by 5 mg/kg subcutaneous injection of testosterone propionate and treatment with water.

The group of benign prostatic hyperplasia+treatment with heat-killed probiotics of *Enterococcus faecalis* (BPH+K_EF) was a benign prostatic hyperplasia induced group prepared by four weeks of daily oral administration of $1.66 \times 10^{12}$ CFU/kg of heat-killed probiotics of *Enterococcus faecalis* EF-2001 ($7.5 \times 10^{12}$ colonies formed), which was killed by heat treatment.

The group of benign prostatic hyperplasia+treatment with probiotics of *Enterococcus faecalis* (BPH+L_EF) was a benign prostatic hyperplasia induced group prepared by four weeks of daily oral administration of $1.66 \times 10^{12}$ CFU/kg of *Enterococcus faecalis* EF-2001 ($1 \times 10^{11}$ colonies formed)

The group of BPH+treatment with finasteride (BPH+Fi) is a benign prostatic hyperplasia induced group prepared by four weeks of daily oral administration of 1 mg/kg of finasteride.

Statistical Analysis

The data were expressed as 'mean±standard error' (n=8).

The statistical analysis was performed by ANOVA, and the results were expressed as ##P<0.01 vs. Con, *P<0.05, **P<0.01 vs BPH.

Experimental Example 1: Analysis of Prostate Weight and Prostate Index

In benign prostatic hyperplasia, changes in body weight and prostate index in rats were measured according to the administration of probiotics and heat-killed probiotics of *Enterococcus faecalis*. The experimental groups were set as shown below, and the prostate index refers to the prostate weight (g)/body weight (100 g) ratio.

Table 1 below shows the initial body weight and final body weight of the rat groups.

TABLE 1

| Item | Con | BPH | BPH + K_EF | BPH + L_EF | BPH + Fi |
|---|---|---|---|---|---|
| Initial body weight (g) | 249.19 ± 1.38 | 249.40 ± 1.51 | 249.26 ± 1.99 | 250.06 ± 1.15 | 248.818 ± 1.24 |
| Final body weight (g) | 317.62 ± 15.42 | 291.42 ± 12.90 | 289.46 ± 13.77 | 296.60 ± 25.58 | 296.934 ± 9.31 |

FIG. 1 is a photograph of the prostate each dissected from the rat groups after the experiment. When visually confirmed, the size of the prostate of the BPH+K_EF treatment group was smaller than that of the BPH+L_EF treatment group.

Figure 2:
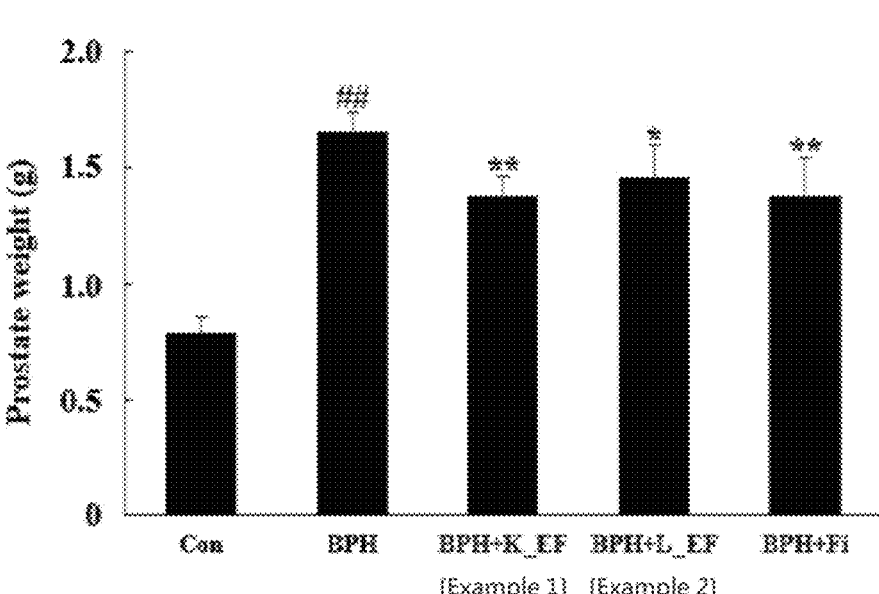
FIG. 2 is a graph comparing the average weight of the prostate according to Experimental Example 1.

FIG. 2 is a graph comparing the average prostate weight among rat groups after the experiment. According to this, the BPH+K_EF treatment group showed a significantly smaller value than the BPH group, the BPH+K_EF treatment group also showed a lower value than the BPH+L_EF treatment group.

Figure 3:
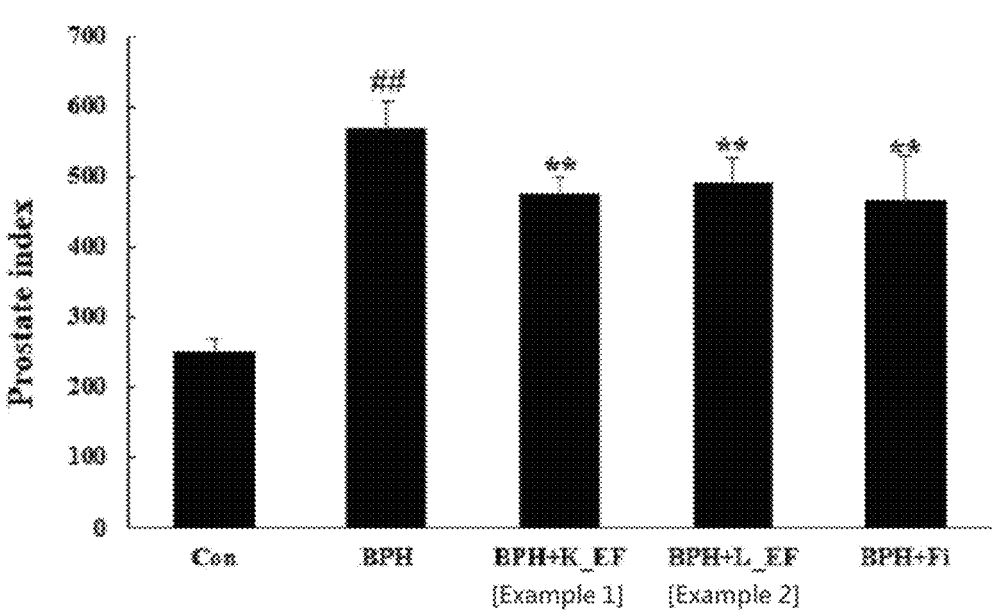
FIG. 3 is a graph comparing the prostate index according to Experimental Example 1.

FIG. 3 is a graph comparing the prostate index of the individual treatment groups, which was calculated based on the results described above. According to this, the BPH+ K_EF treatment group showed a significantly smaller value than the BPH group.

Experimental Example 2: Analysis of Changes in Prostate Histopathology

Figure 4:
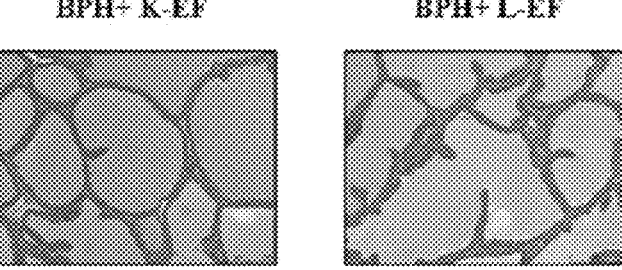
FIG. 4 is a microscopic image of the prostate tissue according to Experimental Example 2.
Figure 4:
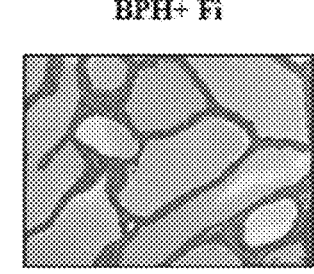

After the end of the experiment, the excised prostate was fixed with 10% neutral buffered formalin for 24 hours and then paraffin-embedded. The embedded tissue was fabricated into a 4 µm-thick section, which was then stained with H&E, encapsulated with an encapsulation solution, and observed by using an optical microscope. FIG. 4 shows a microscope image magnified at 100× magnification.

According to this, the BPH+K_EF treatment group showed significantly improved benign prostatic hyperplasia, compared to the BPH group, and a better improving effect was observed even when compared to the BPH+L_EF treatment group.

Figure 5:
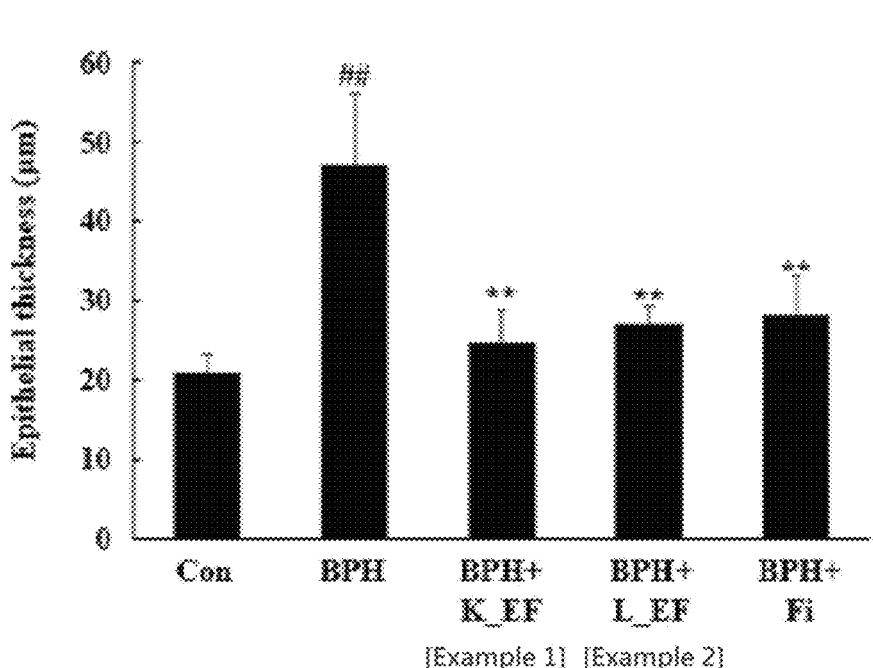
FIG. 5 is a graph comparing the epithelial thickness of the prostate tissue according to Experimental Example 2.

FIG. 5 is a graph showing the results of comparing the epithelial thickness of the prostatic tissue of the individual experimental groups. According to this, the BPH+K_EF treatment group showed a significantly smaller value than the BPH group, and also showed a smaller value than the BPH+L_EF treatment group. Therefore, it was confirmed that when the heat-killed probiotics of *Enterococcus faecalis* was treated, the effect of inhibiting the overgrowth of prostatic epithelial cells was the greatest.

Figure 6:
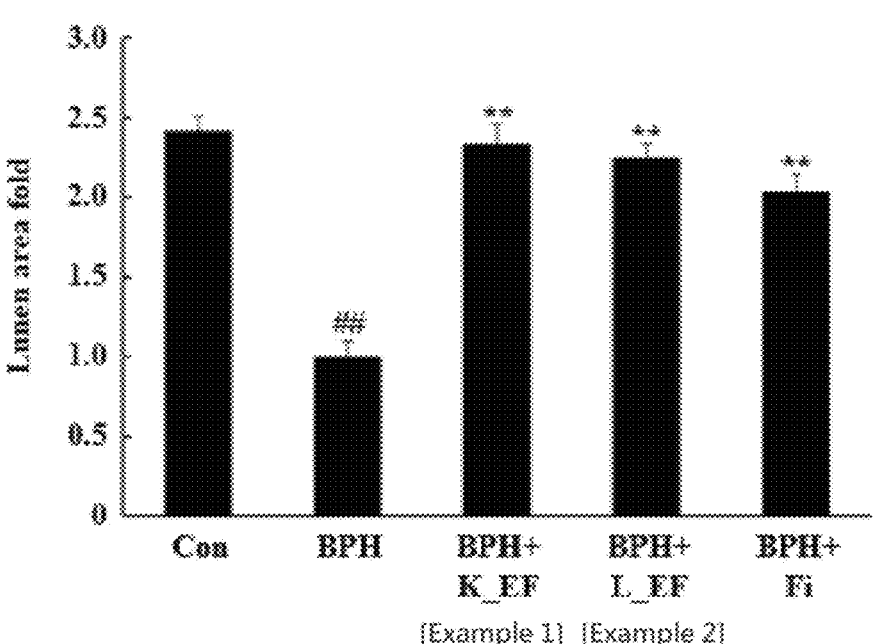
FIG. 6 shows the measurement results of the lumen area fold according to Experimental Example 2.

FIG. 6 shows the measurement results of the luminal area fold in the prostatic tissue of the individual experimental groups. The thicker the epithelial tissue, the smaller the luminal area.

According to this, the BPH+K_EF treatment group showed a significantly larger value than the BPH group, and also showed a larger value than the BPH+L_EF treatment group.

Experimental Example 3: Measurement of Dihydrotestosterone (DHT) Levels

Figure 7:
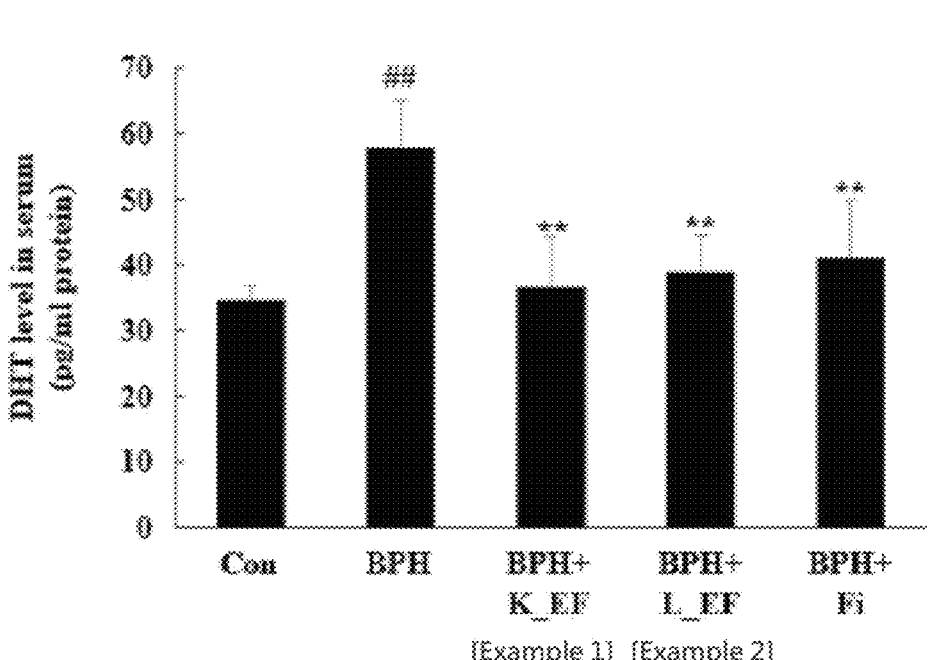
FIG. 7 shows the measurement results of the content of DHT in the prostate according to Experimental Example 3.

Dihydrotestosterone (DHT) is a hormone that enlarges the prostate and thus plays an important role in the onset and deterioration of benign prostatic hyperplasia. To measure the change of DHT, following the end of the 4-week drug administration, the protein was separated from the prostatic tissue that was isolated at the time of sacrifice. Using an ELISA kit (SunLong Biotech Co. (Hangzhou, China) that reacts specifically to DHT, the content of DHT in the prostate was measured according to the method provided by the manufacturer, and the results are shown in FIG. 7.

Figure 8:
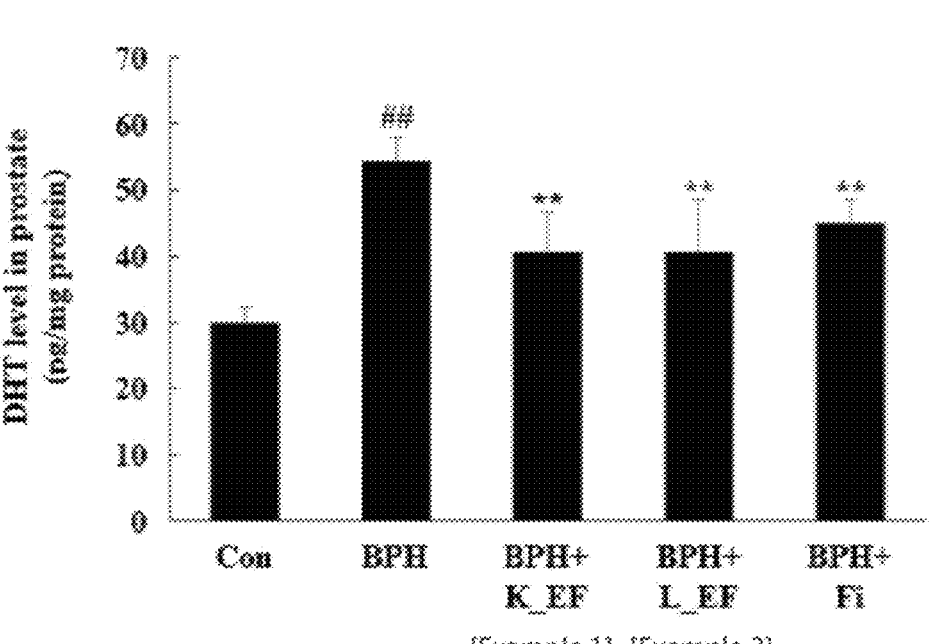
FIG. 8 shows the testosterone measurement results according to Experimental Example 3.

In addition, to check the blood DHT level, the blood separated after the end of the experiment was centrifuged at 12000 rpm for 20 minutes, and the supernatant was taken to measure the testosterone level in serum by using an ELISA. The results are shown in FIG. 8.

According to this, in the group of the treatment with the heat-killed probiotics of *Enterococcus faecalis* (BPH+ K_EF) and the group of the treatment with the probiotics (BPH+L_EF), the level was significantly lower than that of the BPH group, and the level was further lowered in the heat-killed probiotics treatment group than in the probiotics treatment group.

Experimental Example 4: Hepatotoxicity Analysis

Figure 9:
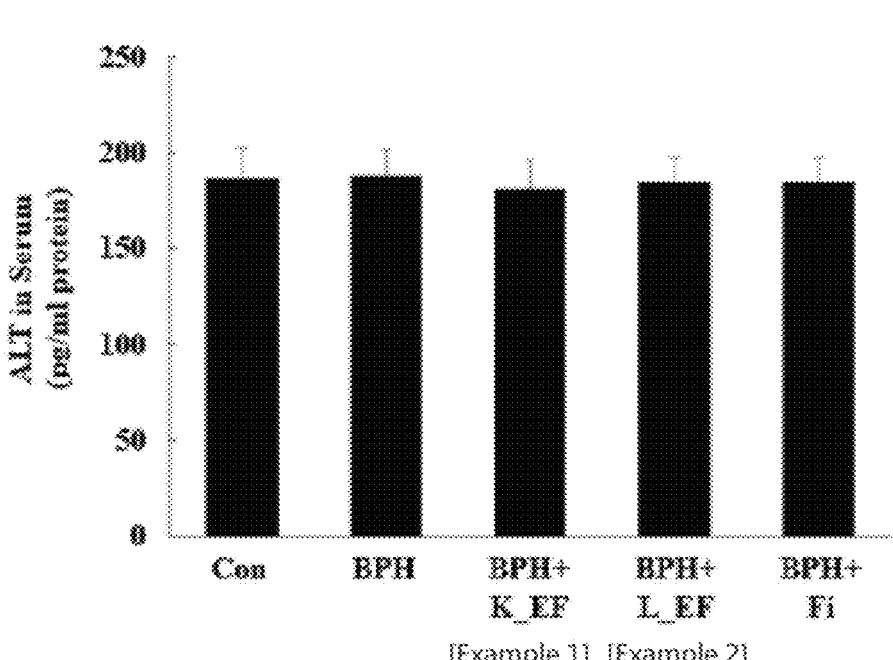
FIG. 9 shows the ALT measurement results according to Experimental Example 4.
Figure 10:
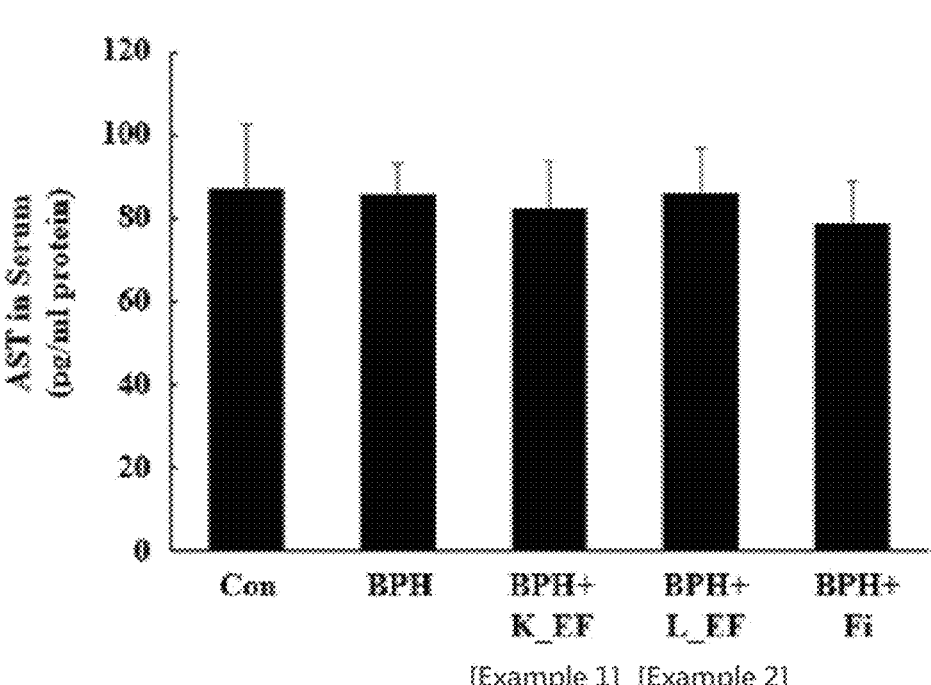
FIG. 10 shows the AST measurement results according to Experimental Example 4.

In order to check the toxicity of the individual experimental groups in the benign prostatic hyperplasia animal model, the blood separated after the end of the experiment was centrifuged at 12,000 rpm for 20 minutes, and the supernatant was taken to measure in serum ALT (alanine transaminase) and AST (aspartate transaminase), which are the common indexes of hepatotoxicity. FIG. 9 shows the ALT measurement results, and FIG. 10 shows the AST measurement results.

According to this, no significant change was observed in ALT and AST levels in all the experimental groups compared to the normal group. Therefore, it was confirmed that the group of the treatment with the heat-killed probiotics of *Enterococcus faecalis* (BPH+K_EF) and the group of the treatment with the probiotics (BPH+L_EF) were free from hepatotoxicity.

Experimental Example 5: Measurement of ER, AR and PSA Expression Levels

To investigate the efficacy of probiotics and heat-killed probiotics of *Enterococcus faecalis*, the expression level of AR (androgen receptor) signal-related factors was measured in the prostatic tissue of the benign prostatic hyperplasia induced rats.

Figure 11:
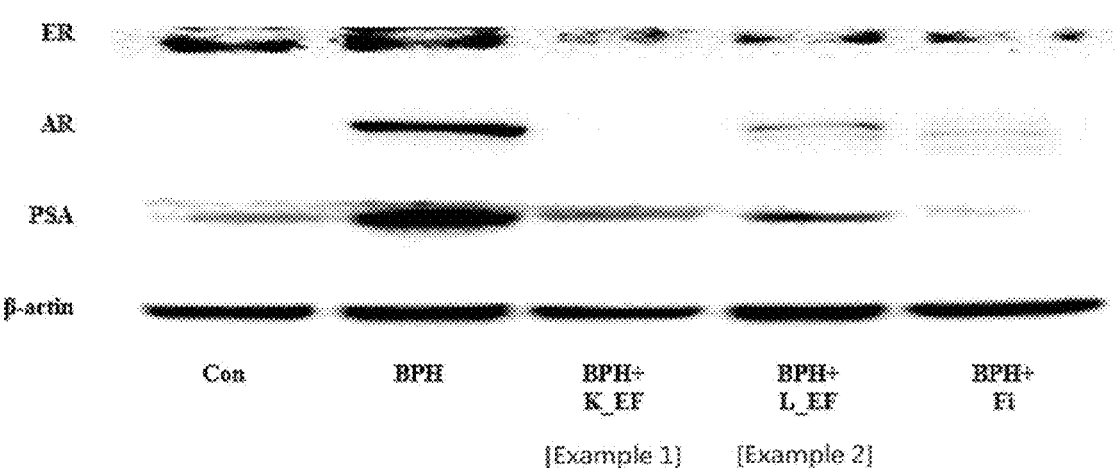
FIGS. 11 to 14 show the measurement results of the expression levels of ER, AR and PSA according to Experimental Example 5.
Figure 12:
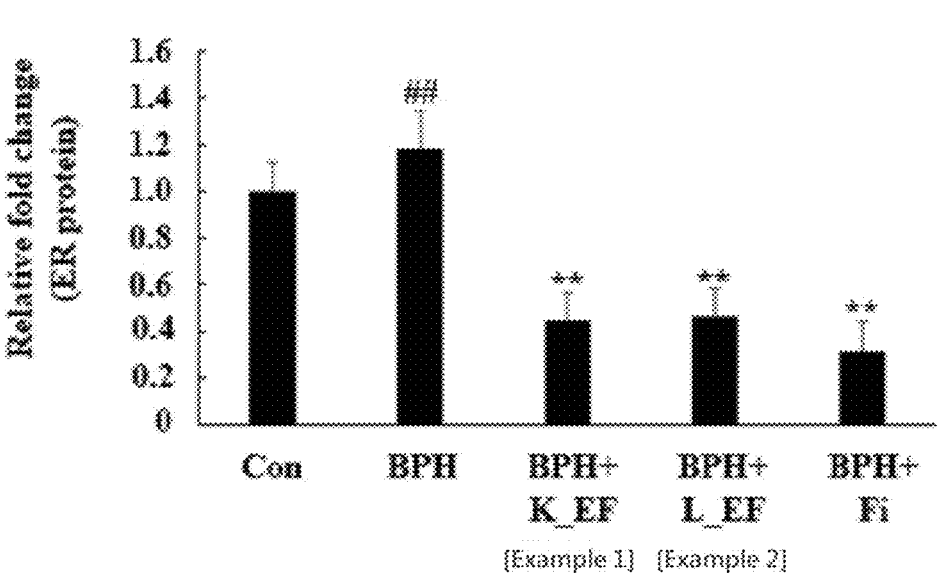
Figure 13:
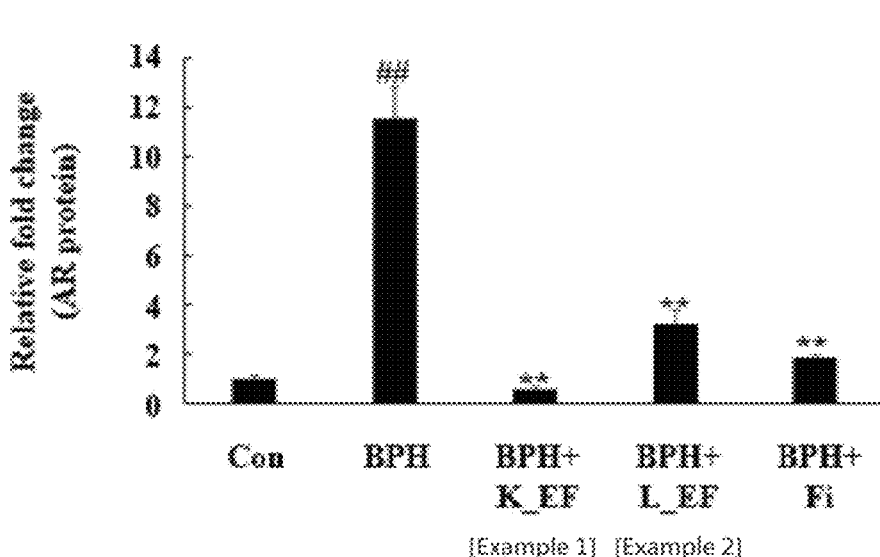
Figure 14:
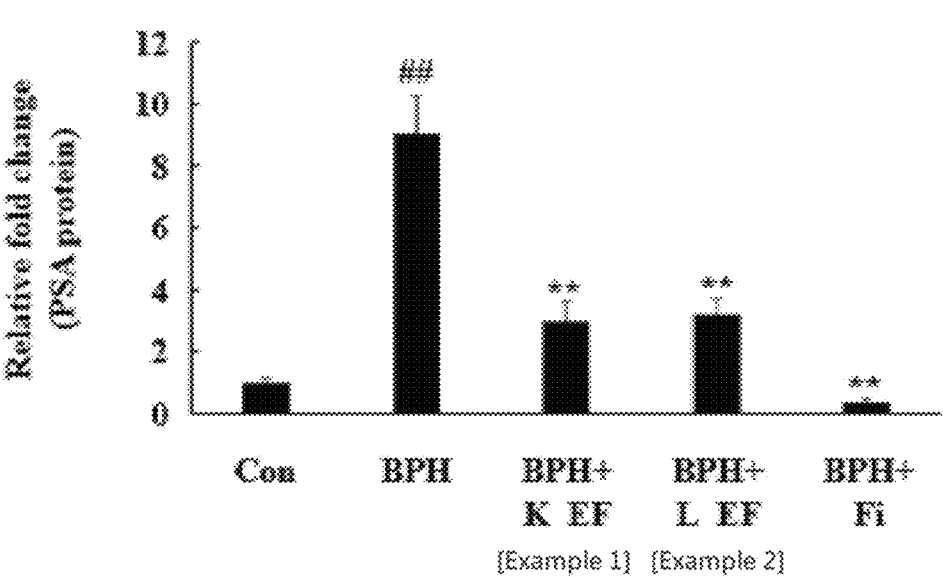

FIG. 11 shows the results of the Western blot showing the expression of ER (estrogen receptors), AR (androgen receptor), and PSA (prostate specific antigen) proteins in the prostatic tissue, and FIGS. 12, 13 and 14 are graphs showing the analytical results of the ER, AR, and PSA concentrations, respectively, obtained by using the ImageJ software program from the results of the Western blot.

According to this, the expression levels of ER, AR and PSA were significantly lower in both the group of the treatment with the heat-killed probiotics of *Enterococcus faecalis* (BPH+K_EF) and the group of the treatment with the probiotics (BPH+L_EF) than in the benign prostatic hyperplasia induced group (BPH). In particular, the AR (androgen receptor) expression level was significantly lower in the group of the treatment with the heat-killed probiotics of *Enterococcus faecalis* (BPH+K_EF) than in the group of the treatment with the probiotics (BPH+L_EF), which confirmed that the treatment with heat-killed probiotics is more effective than the treatment with probiotics of *Enterococcus faecalis*.

The Experimental Examples described above confirmed the effect of reducing the expression level of androgen receptor signal-related factors on the benign prostatic hyperplasia induced groups. However, considering that the androgenetic alopecia is caused by a mechanism that is similar to the induction of benign prostatic hyperplasia, it is predicted that the probiotics or heat-killed probiotics of *Enterococcus faecalis* of the present invention is also effective in preventing alopecia.

Experimental Example 6: Analysis of Apoptosis
Factor Expression Level

To examine the efficacy of heat-killed probiotics and probiotics of *Enterococcus faecalis*, the expression level of the apoptosis factors was measured in the prostatic tissue of the benign prostatic hyperplasia induced rats.

Figure 15:
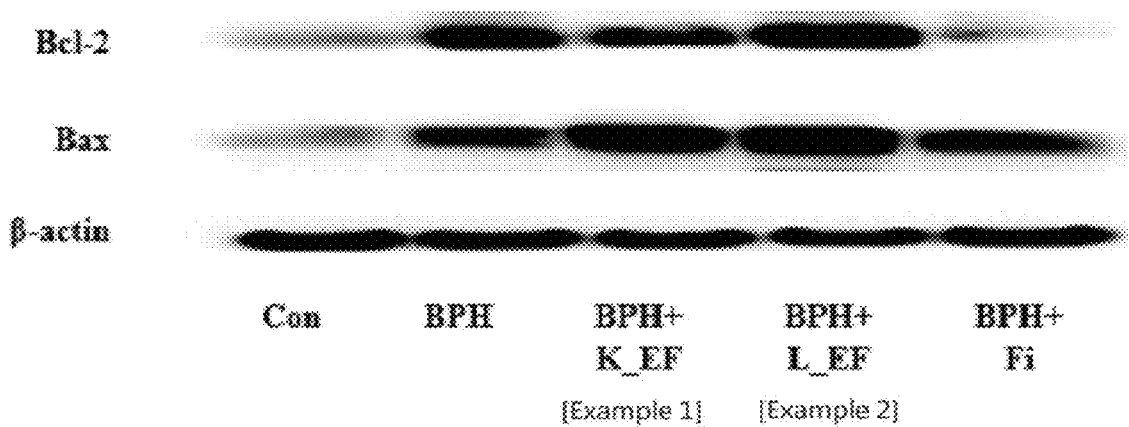
FIGS. 15 and 16 show the measurement results of the expression levels of the apoptosis inducing factors according to Experimental Example 6.
Figure 16:
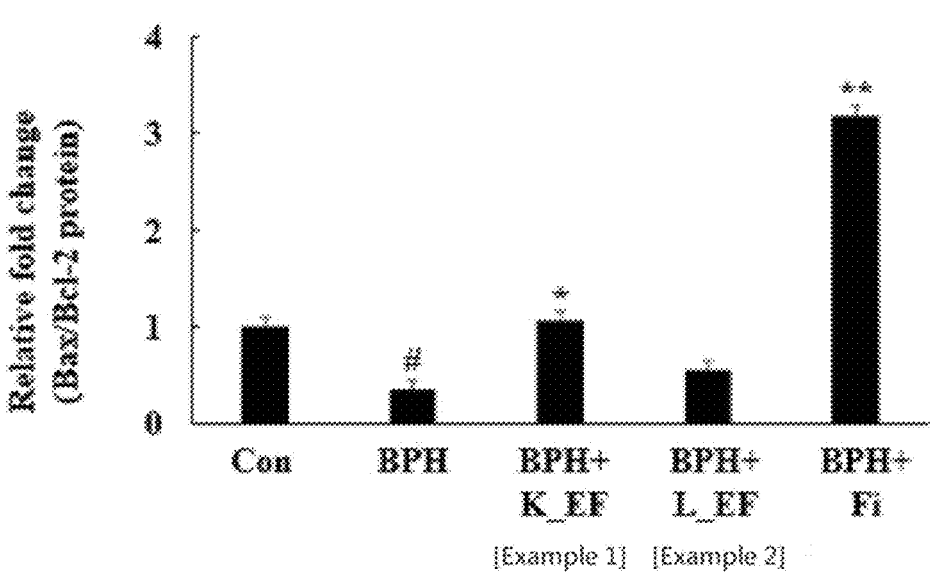

FIG. 15 shows the results of Western blot showing the expression of Bcl-2 (B-cell lymphoma 2), which is an apoptosis inhibiting factor, and the expression of Bax, which is an apoptosis inducing factor, in the prostatic tissue. FIG. 16 shows the analytical results of the Bax/Bcl-2 concentration ratio obtained by using the ImageJ software program. According to this, the group of the treatment with the heat-killed probiotics of *Enterococcus faecalis* (BPH+ K_EF) showed a significantly higher value than the benign prostatic hyperplasia-induced group (BPH).

Experimental Example 7: Analysis of Expression
Level of Cell Growth Factors

In order to investigate the efficacy of the heat-killed probiotics and probiotics of *Enterococcus faecalis*, the expression level of cell proliferation factors in the prostatic tissue of the benign prostatic hyperplasia-induced rats was measured.

Figure 17:
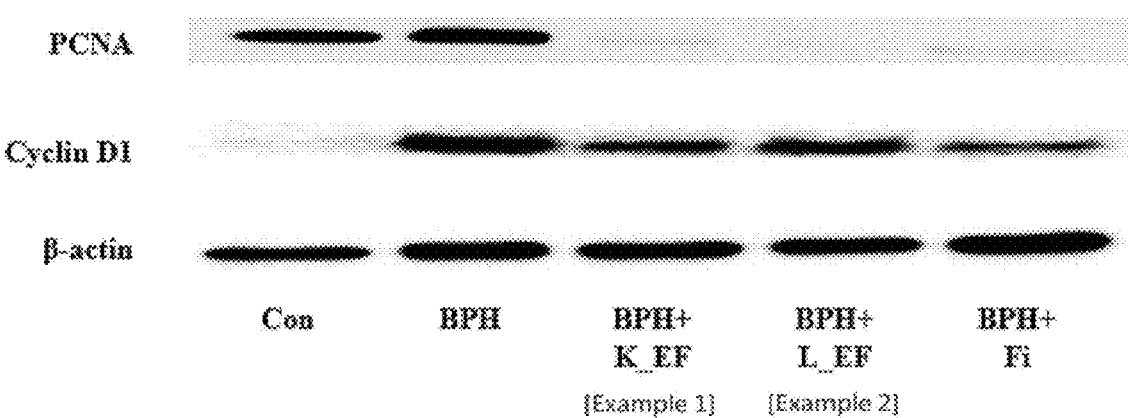
FIGS. 17 to 19 show the measurement results the expression levels of the cell proliferation factors according to Experimental Example 7.
Figure 18:
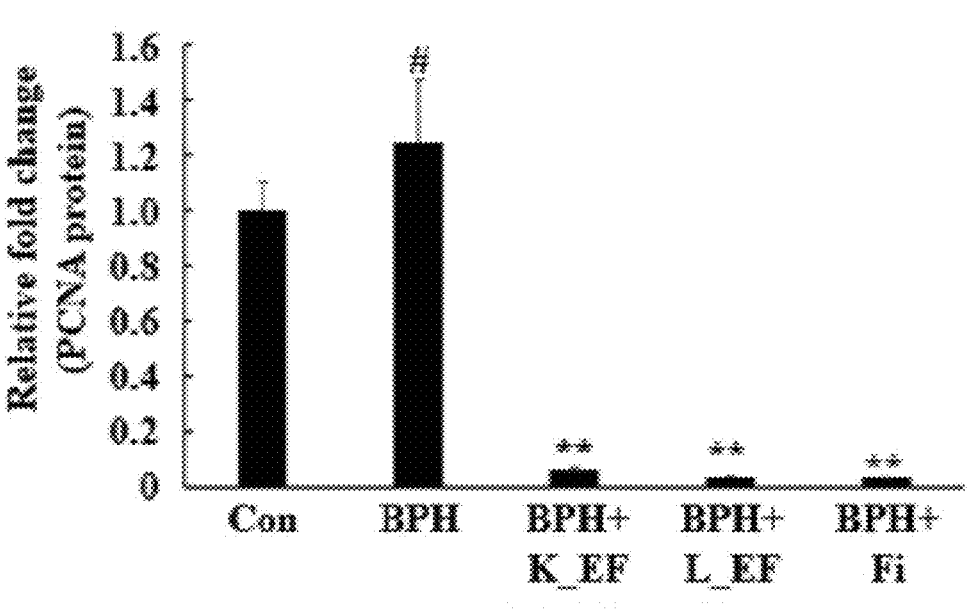
Figure 19:
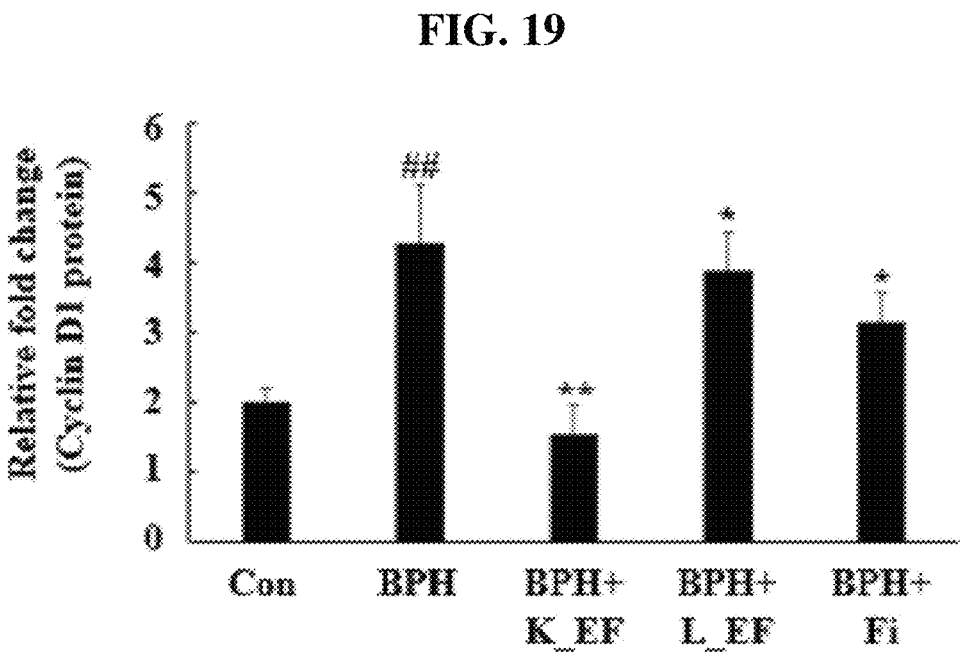

FIG. 17 shows the results of the Western blot showing the expression of PCNA (proliferating cell nuclear antigen) and Cyclin D1 protein, which are cell proliferation factors, in the prostatic tissue, and FIGS. 18 and 19 show the analytical results of PCNA and Cyclin D1 concentrations obtained by using the ImageJ Software, respectively. According to this, the group of the treatment with the heat-killed probiotics of

*Enterococcus faecalis* (BPH+K_EF) and the group of the treatment with the probiotics (BPH+L_EF) showed a significantly lower value than the benign prostatic hyperplasia induced group (BPH). In particular, the expression level of Cyclin D1 was significantly lower in the group of the treatment with the heat-killed probiotics of *Enterococcus faecalis* (BPH+K_EF) than in the group of the treatment with the probiotics (BPH+L_EF) or the group of the finasteride treatment (BPH+Fi).

In the above, Examples of the present invention have been described, but one of ordinary skill in the art can variously modify and change the prevent invention by supplementing, changing, deleting or adding features within the scope that does not depart from the principles of the present invention described in the claims, and this will also be included within the scope of the present invention.

The invention claimed is:

1. A method of treating benign prostatic hyperplasia (BPH) in a subject, the method comprising orally administering to the subject a composition comprising heat-killed probiotics of *Enterococcus faecalis* EF-2001 as an active ingredient.

2. The method of claim 1, wherein the administering reduces expression of an androgen receptor (AR) signaling factor selected from estrogen receptors (ER), androgen receptor (AR), and prostate specific antigen (PSA).

3. The method of claim 1, wherein the administering increases expression of Bax and/or decreases expression of Bcl-2 in prostate tissue.

4. The method of claim 1, wherein the administering reduces expression of a proliferation marker selected from proliferating cell nuclear antigen (PCNA) and Cyclin D1.

* * * * *